US00PP15450P2

(12) United States Plant Patent
Vandenberg

(10) Patent No.: US PP15,450 P2
(45) Date of Patent: Dec. 21, 2004

(54) ***CARNATION* PLANT NAMED 'YODER LADY'**

(50) Latin Name: *Dianthus caryophyllus*
Varietal Denomination: Yoder Lady

(75) Inventor: Cornelis P. Vandenberg, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 10/818,358

(22) Filed: Apr. 5, 2004

(51) Int. Cl.[7] ..... A01H 5/00
(52) U.S. Cl. ..... Plt./273
(58) Field of Search ..... Plt./273

*Primary Examiner*—Kent Bell
(74) *Attorney, Agent, or Firm*—C. A. Whealy

(57) ABSTRACT

A distinct cultivar of *Carnation* plant named 'Yoder Lady', characterized by its orange-colored flowers with occasional red-colored streaks and splashes; early and freely flowering habit with about 12 to 14 flowers per flowering stem; fragrant flowers; good postproduction longevity with flowers maintaining good substance and color for about ten days in an interior environment after shipping; and resistance to *Fusarium oxysporum*.

2 Drawing Sheets

Botanical classification: *Dianthus caryophyllus* cultivar Yoder Lady.

BACKGROUND OF THE INVENTION

The present invention relates to a new and distinct cultivar of *Carnation* plant, botanically known as *Dianthus caryophyllus* and hereinafter referred to by the name 'Yoder Lady'.

The new *Carnation* is a product of a planned breeding program conducted by the Inventor in Salinas, Calif., and Suba, Cundinamarca, Colombia, South America. The objective of the breeding program is to create new cut *Carnation* cultivars having long flowering stems, early flowering, attractive flower color, and good flower form and substance.

The new *Carnation* originated from a cross-pollination made by the Inventor in 1994, in Salinas, Calif., of a proprietary selection of *Carnation* identified as code number 0110, not patented, as the female, or seed, parent, with the *Carnation* cultivar Jazz, disclosed in U.S. Plant Pat. No. 10,121, as the male, or pollen, parent.

The cultivar Yoder Lady was discovered and selected by the Inventor as a flowering plant within the progeny of the stated cross-pollination in a controlled environment in Suba, Cundinamarca, Colombia, South America in October, 1995. The selection of this plant was based on its flower color and good flower form and substance.

Asexual reproduction of the new *Carnation* by terminal cuttings in Suba, Cundinamarca, Colombia, South America since November, 1995, has shown that the unique features of this new *Carnation* are stable and reproduced true to type in successive generations.

SUMMARY OF THE INVENTION

The cultivar Yoder Lady has not been observed under all possible environmental conditions. The phenotype may vary somewhat with variations in environment such as temperature and light intensity without, however, any variance in genotype.

The following traits have been repeatedly observed and are determined to be the unique characteristics of 'Yoder Lady'. These characteristics in combination distinguish 'Yoder Lady' as a new and distinct cultivar of *Carnation:*

1. Orange-colored flowers with occasional random orange red-colored streaks and splashes.
2. Early and freely flowering habit with about 12 to 14 flowers per flowering stem.
3. Fragrant flowers.
4. Good postproduction longevity with flowers maintaining good substance and color for about ten days in an interior environment after shipping.
5. Resistance to *Fusarium oxysporum.*

Plants of the new *Carnation* can be compared to plants of the female parent selection. In side-by side comparisons conducted in Suba, Cundinamarca, Colombia, South America, plants of the new *Carnation* and female parent selection differed primarily in flower coloration as plants of the female parent selection had pink-colored flowers.

Plants of the new *Carnation* can be compared to plants of the male parent, the cultivar Jazz. In side-by side comparisons conducted in Suba, Cundinamarca, Colombia, South America, plants of the new *Carnation* and the cultivar Jazz differed in the following characteristics:

1. Plants of the new *Carnation* flowered one to two weeks earlier than plants of the cultivar Jazz.
2. Plants of the new *Carnation* and the cultivar Jazz differed in flower coloration as flowers of plants of the cultivar Jazz had more red-colored streaks and splashes than plants of the new *Carnation.*

BRIEF DESCRIPTION OF THE PHOTOGRAPHS

The accompanying colored photographs illustrate the overall appearance of the new *Carnation,* showing the colors as true as it is reasonably possible to obtain in colored reproductions of this type. Colors in the photographs may differ slightly from the color values cited in the detailed botanical description, which accurately describe the colors of the new *Carnation.*

The photograph on the first sheet comprises a side perspective view of a typical flowering stem of 'Yoder Lady' grown as a spray-type cut Carnation.

The photograph on the second sheet comprises a close-up view of typical flowers of 'Yoder Lady'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Madrid, Cundinamarca, Colombia, South America under conditions which approximate commercial practice in a single-layer polyethylene-covered greenhouse. Four-week old rooted cuttings were planted in ground beds and pinched about three to four weeks later. During the production time, day temperatures ranged from 19 to 24° C.; night temperatures ranged from 4 to 12° C.; and light levels ranged from 3,000 to 5,000 foot-candles. Measurements and numerical values represent averages for six to ten typical flowering stems about 26 weeks after planting.

Botanical classification: *Dianthus caryophyllus* cultivar Yoder Lady.

Commercial classification: Miniature spray-type cut *Carnation.*

Parentage:

*Female, or seed, parent.*—Proprietary selection of *Dianthus caryophyllus* identified as code number 0110, not patented.

*Male, or pollen, parent.*—*Dianthus caryophyllus* cultivar Jazz, disclosed in U.S. Plant Pat. No. 10,121.

Propagation:

*Type.*—Terminal tip cuttings.

*Time from sticking unrooted cuttings to planting.*—About four weeks.

*Root description.*—Fine, freely-branching.

Plant description:

*Flowering stem description.*—Aspect: Erect. Strength: Very strong, flexible. Length: About 85 cm. Diameter: About 7 mm. Internode length, between basal flower and next lowest internode: About 5.4 cm. Texture: Smooth. Color: Close to 144A, overlain with waxy bloom, close to 188B to 188C.

*Foliage description.*—Arrangement: Opposite; sessile. Aspect: Slightly concave; mostly upright, approximately 45° angle from vertical to eventually reflexed. Length: About 13.3 cm. Width: About 1.1 cm. Shape: Linear. Apex: Sharply acute to acuminate. Margin: Entire. Texture: Tough, leathery; waxy. Color: Developing foliage, upper and lower surfaces: Close to 147A, overlain with waxy bloom, close to 188A to 188B. Fully developed foliage, upper and lower surfaces: Close to 147A, overlain with waxy bloom, close to 188A to 188B.

Flowering description:

*Appearance.*—Single hemispherical flowers arranged in sprays. Freely flowering, with potentially one flower developing at every node; usually about 12 to 14 flowers developing per flowering stem.

*Flowering response.*—Year-round under greenhouse conditions; plants flower about 26 weeks after planting rooted cuttings.

*Postproduction longevity.*—Good postproduction longevity with flowers maintaining good substance and color for about ten days in an interior environment after shipping. Flowers persistent.

*Fragrance.*—Moderately fragrant; spicy, clove-like.

*Flower size.*—Diameter: About 5.3 cm. Depth (height): About 4.4 cm.

*Flower buds* (*at stage of showing color*).—Length: About 3.1 cm. Diameter: About 1.1 cm. Shape: Oblong. Color: Towards the apex, close to 3D; towards the base, close to 146A.

*Petals/petaloids.*—Quantity per flower: About 32, imbricate. Length: About 4.5 cm. Width: About 2.1 cm. Shape: Roughly spatulate. Apex: Roughly rounded; finely serrated giving a fringed appearance, undulate. Lateral margins: Entire. Texture: Velvety, smooth, glabrous. Color, when opening and fully opened, upper and lower surfaces: Towards the base, close to 155A overlain with close to 144A; center, close to 155A; towards the apex, 155A overlain with close to 34A; occasional random streaks and splashes, close to 42A; iridescent.

*Sepals.*—Quantity: About six, fused. Length: About 2.8 cm. Width: About 8 mm. Calyx diameter: Apex: About 1.5 cm. Base: About 1.2 cm. Shape: Roughly ovate. Apex: Acuminate. Texture: Tough, leathery; smooth; waxy, longitudinally ridged. Resistance to splitting: Very good, calyxes rarely split. Color: Upper surface: Close to 195A to 195B. Lower surface: Close to 146A to 146B.

*Reproductive organs.*—Androecium: Stamen number: About eight; most are transformed into petaloids. Stamen length: About 2 cm. Stamen color: Close to 155D. Anther size: About 2 mm by 4 mm. Anther shape: Oblong. Anther color: Close to 9D. Pollen: None observed. Gynoecium: Pistil quantity: Four. Pistil length: About 1.2 cm. Color: Close to 155D. Ovary size: About 5.5 mm by 7 mm. Ovary color: Close to 144A to 144B.

*Seed/fruit.*—Seed and fruit production have not been observed.

Disease/pest resistance: Plants of the new *Carnation* planted in soils heavily infested with *Fusarium oxysporum* have been observed to be highly resistant to *Fusarium oxysporum.* Plants of the new *Carnation* have not been observed to be resistant to other pathogens and pests common to *Carnations.*

It is claimed:

1. A new and distinct cultivar of *Carnation* plant named 'Yoder Lady', as illustrated and described.

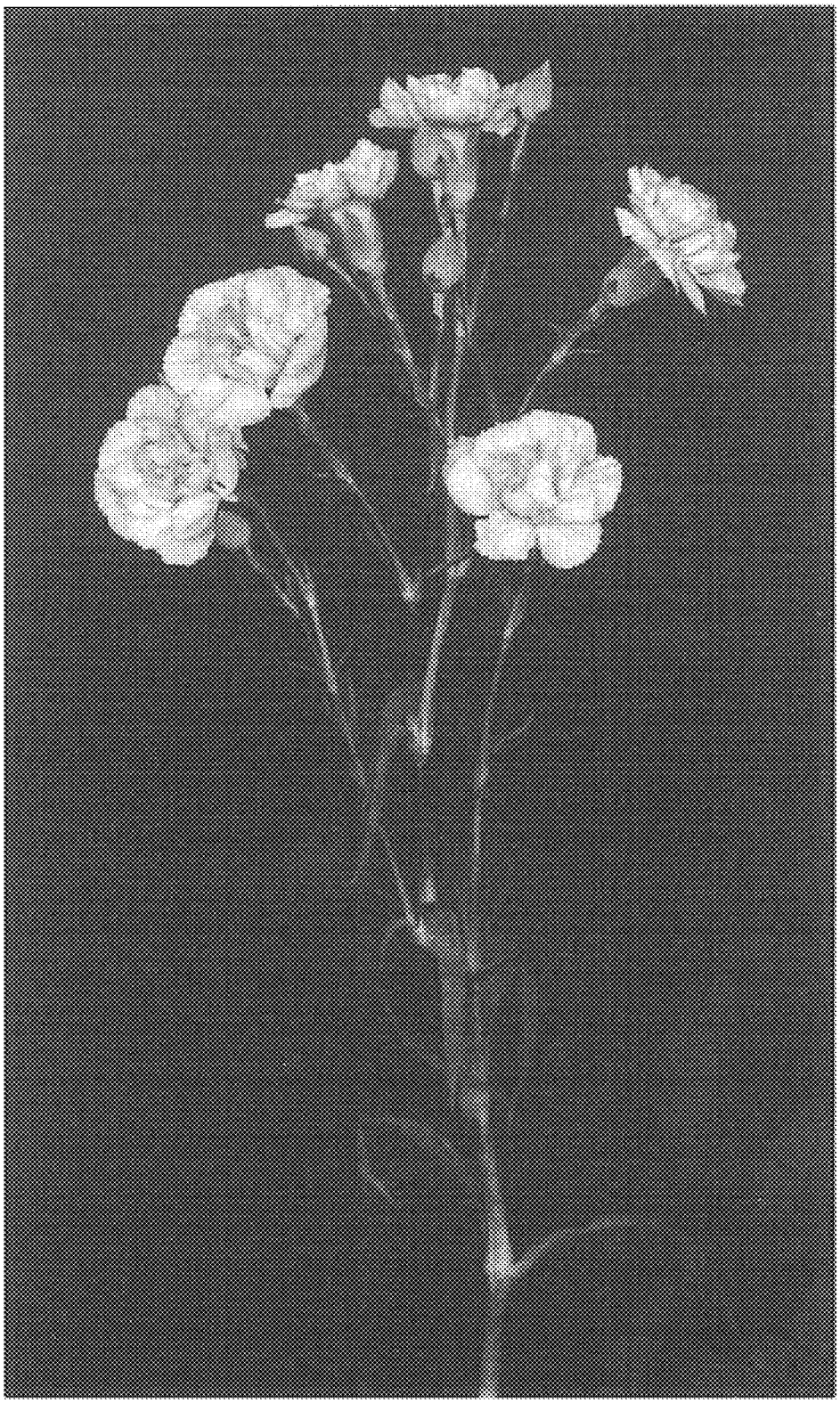

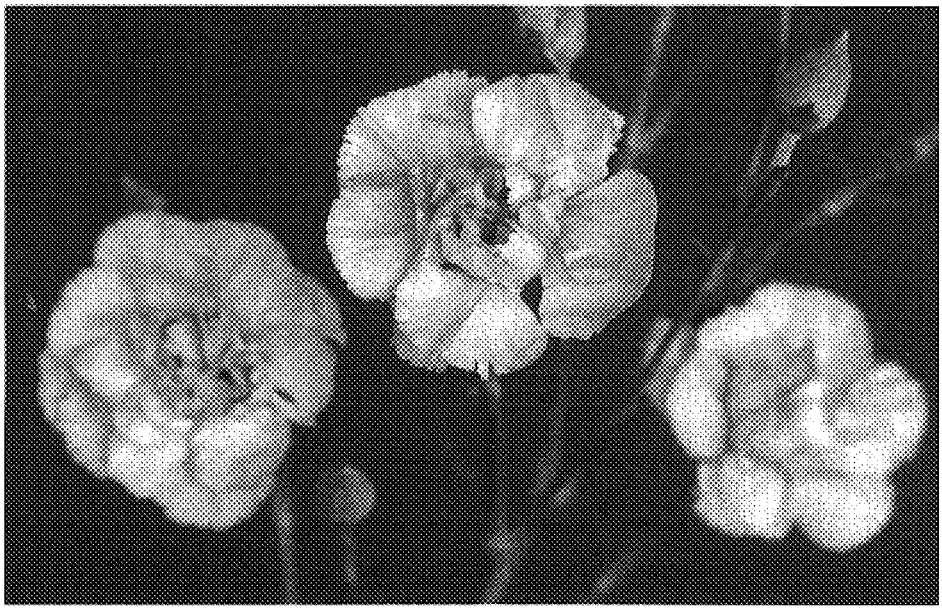

* * * * *